United States Patent [19]

Morrow et al.

[11] Patent Number: 5,530,180
[45] Date of Patent: Jun. 25, 1996

[54] HYBRID CORN PLANT AND SEED (3189)

[75] Inventors: Donald L. Morrow, Garden City, Kans.; Stephen W. Noble, Johnston, Iowa

[73] Assignee: Pioneer Hi-Bred International, Inc., Des Moines, Iowa

[21] Appl. No.: 402,019

[22] Filed: Aug. 30, 1989

[51] Int. Cl.$^6$ .............................. A01H 5/00; A01H 4/00; C12N 5/04
[52] U.S. Cl. ................. 800/200; 800/250; 800/DIG. 56; 435/240.4; 435/240.49; 435/240.5
[58] Field of Search ................................... 800/200, 250, 800/DIG. 58; 47/58, DIG. 1; 435/240.49, 240.40

[56] References Cited

U.S. PATENT DOCUMENTS

| | | | |
|---|---|---|---|
| 4,629,819 | 12/1986 | Lindsey | 800/1 |
| 4,654,466 | 3/1987 | Lindsey | 800/1 |

OTHER PUBLICATIONS

Duncan, et al. "The Production of Callus Capable of Plant Regeneration from Immature Embryos of Numerous Zea mays Genotypes", Planta (1985) 165:322–332.
Songstad, et al. "Effect of ACC (1-aminocyclopropane-1-carboxylic acid), Silver Nitrate, and Norbornadiene on Plant Regeneration from Maize Callus Cultures", Plant Cell Reports 7:262–265 (1988).
K. V. Rao, et al. "Somatic Embryogenesis in Glume Callus Cultures", Maize Genetics Cooperation Newsletter (1986). vol. 60.
Conger, B. V., et al. "Somatic Embryogenesis from Cultured Leaf Segments of Zea Mays", Plant Cell Reports 6:345–347 (1987).
Raman, K., et al., "Propagation of Zea mays L. by Shoot Tip Culture: A Feasibility Study", Ann. Bot., 45, 183–189, 1980.
Walden, D. B., et al., "Maize Meristem Culture & Recovery of Mature Plants", Maydica, 34 (1989): 263–275.
Irish, Erin E., et al., "Development of Maize Plants From Cultured Shoot Apices", Planta, 175:9–12, (1988).
Benzin et al., (1986) Core Histories of Genetic Variability in Vitro Oats & Mayo. In Cell Culture & Somatic Cell genetic of Plants vol. #3. pp. 435–448.
Sass (1977) "Morphology". In Corn & Corn Improvement. ASA Publication. Madison Wisconson. pp. 89–110. Editor G. F. Sprague.
Green et al (1982) In Maze for Biological Research Editor. W. Sheridon, pp. 367–372. Ph. Mol. Bio. Assoc. Le Press N. Dakoter.
Sprague et al. (1977) In Corn and Corn Improvement. Ed. Sprague et al. Am. Soc. Agron. Madison WI pp. 319–323.

Primary Examiner—Gary Benzion
Attorney, Agent, or Firm—Pioneer Hi-Bred International, Inc.

[57] ABSTRACT

According to the invention, there is provided a hybrid corn plant, designated as 3189, produced by crossing two Pioneer Hi-Bred International, Inc. proprietary inbred corn lines. This invention thus relates to the hybrid plant 3189, and variants, mutants, and modifications of Pioneer hybrid 3189. This hybrid corn plant is characterized by superior qualities of high yield for its maturity, wide adaptation, short plant stature, good standability, very good drought tolerance, excellent stay green, and it responds well for yield to higher planting rates.

5 Claims, No Drawings

HYBRID CORN PLANT AND SEED (3189)

FIELD OF THE INVENTION

This invention is in the field of plant breeding, specifically hybrid corn breeding.

BACKGROUND OF THE INVENTION

The goal of plant breeding is to combine in a single variety/hybrid various desirable traits of the parental lines. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and fruit size, is important.

Field crops are bred through techniques that take advantage of the plant's method of pollination. A plant is self-pollinating if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous lines produce a uniform population of hybrid plants that may be heterozygous for many gene loci. A cross of two plants each heterozygous at a number of gene loci will produce a population of hybrid plants that differ genetically and will not be uniform. Corn plants (Zea mays L.) can be bred by both self-pollination and cross-pollination techniques. Corn has male flowers, located on the tassel, and female flowers, located on the ear, on the same plant. Natural pollination occurs in corn when wind blows pollen from the tassels to the silks that protrude from the tops of the incipient ears.

The development of corn hybrids requires the development of homozygous inbred lines, the crossing of these lines, and the evaluation of the crosses. Pedigree breeding and recurrent selection breeding methods are used to develop inbred lines from populations. Breeding programs combine desirable traits from two or more inbred lines or various broad-based sources into breeding pools from which new inbred lines are developed by selfing and selection of desired phenotypes. The new inbreds are crossed with other inbred lines and the hybrids from these crosses are evaluated to determine which have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced. $F_1 \rightarrow F_2$; $F_2 \rightarrow F_3$; $F_3 \rightarrow F_4$; $F_4 \rightarrow F_5$, etc.

A hybrid corn variety is the cross of two inbred lines, each of which may have one or more desirable characteristics lacked by the other or which complement the other. The hybrid progeny of the first generation is designated $F_1$. In the development of hybrids only the $F_1$ hybrid plants are sought. The $F_1$ hybrid is more vigorous than its inbred parents. This hybrid vigor, or heterosis, can be manifested in many ways, including increased vegetative growth and increased yield.

The development of a hybrid corn variety involves three steps: (1) the selection of superior plants from various germplasm pools; (2) the selfing of the superior plants for several generations to produce a series of inbred lines, which although different from each other, each breed true and are highly uniform; and (3) crossing the selected inbred lines with unrelated inbred lines to produce the hybrid progeny ($F_1$). During the inbreeding process the vigor of the lines decreases. Vigor is restored when two unrelated inbred lines are crossed to produce the hybrid progeny ($F_1$). An important consequence of the homozygosity and homogeniety of the inbred lines is that the hybrid between any two inbreds will always be the same. Once the inbreds that give the best hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid, is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock.

Hybrid corn seed can be produced by manual detasseling. Alternate strips of two inbred varieties of corn are planted in a field, and the pollen-bearing tassels are removed from one of the inbreds (female). Providing that there is sufficient isolation from sources of foreign corn pollen, the ears of the detasseled inbred will be fertilized only from pollen from the other inbred (male), and the resulting seed is therefore hybrid and will form hybrid plants.

The laborious detasseling process can be avoided by using cytoplasmic male-sterile (CMS) inbreds. Plants of a CMS inbred are fertilized with pollen from another inbred that is not male-sterile. Pollen from the second inbred can contribute genes that make the hybrid plants male-fertile. Usually seed from detasseled normal corn and CMS produced seed of the same hybrid is blended to insure that adequate pollen loads are available for fertilization when the hybrid plants are grown.

Corn is an important and valuable field crop. Thus, a continuing goal of plant breeding is to develop stable high yielding corn hybrids that are agronomically sound. The reasons for this goal are obvious: to maximize the amount of grain produced on the land used and to supply food for both animals and humans.

SUMMARY OF THE INVENTION

According to the invention, there is provided a hybrid corn plant, designated as 3189, produced by crossing two Pioneer Hi-Bred International, Inc. proprietary inbred corn lines. This invention thus relates to the hybrid seed 3189, the hybrid plant produced from the seed, and variants, mutants, and trivial modifications of hybrid 3189. This hybrid corn plant is characterized by superior qualities of high yield for maturity and wide adaptation. It has short plant stature, good standability, very good stay green and drought tolerance, and responds well to high planting densities.

DEFINITIONS

In the description and examples that follow, a number of terms are used herein. In order to provide a clear and consistent understanding of the specification and claims, including the scope to be given such terms, the following definitions are provided:

BAR PLT=BARREN PLANTS. This is the number of plants per plot that were not barren (lack ears).

B/STK=BRITTLE STALKS RATING. This is a 1–9 rating where a 1, 5, and 9 represent serious, average, and little or no potential for brittle stalk breakage.

BRT STK=BRITTLE STALKS. This is a measure of the stalk breakage near the time of pollination, and is an indication of whether a hybrid would snap or break near the time of flowering under severe winds. Data are presented as percentage of plants that did not snap.

BU ACR=YIELD (BUSHELS/ACRE). Actual yield of the grain at harvest adjusted to 15.5% moisture. ABS is in absolute terms and % MN is percent of the mean for the experiments in which the hybrid was grown.

COB SC=COB J COB SCORE. The cob score is a rating of how well the grain is shelled off the cob and how badly the cob is broken up going through the combine. This is given as a 1 to 9 score with 9 being very good. A high score indicates that the grain shells off of the cob well, and the cob does not break.

D/D=DRYDOWN. This represents the relative rate at which a hybrid will reach acceptable harvest moisture compared to other hybrids on a 1–9 rating scale. A high score indicates a hybrid that dries relatively fast while a low score indicates a hybrid that dries slowly.

D/E=DROPPED EARS RATING. This is a 1–9 rating where a 1, 5, and 9 represent serious, average, and little or no ear droppage potential, respectively.

DRP EAR=DROPPED EARS. This is a measure of the number of dropped ears per plot and represents the percentage of plants that did not drop ears prior to harvest.

D/T=DROUGHT TOLERANCE. This represents a 1–9 rating for drought tolerance, and is based on data obtained under stress conditions. A high score indicates good drought tolerance and a low score indicates poor drought tolerance.

E/HT=EAR HEIGHT RATING. This is a 1–9 rating with a 1, 5, and 9 representing a very short, average, and very tall hybrid, respectively.

EAR HT=EAR HEIGHT. The ear height is a measure from the ground to the top developed ear node attachment and is measured in inches.

ESC=EARLY STAND COUNT RATING. This is a 1–9 rating with a 1, 5, and 9 representing very poor, average, and very good stand establishment in the spring.

EST CNT=EARLY STAND COUNT. This is a measure of the stand establishment in the spring and represents the number of plants that emerge on a per plot basis for the hybrid.

GDU BL=GDU TO BLACKLAYER. This is the number of growing degree units required for the hybrid to reach blacklayer from the time that it was planted. Growing degree units are calculated by the Barger Method, where the heat units for a 24-hour period are:

$$GDU = \frac{(Max. + Min.)}{2} - 50$$

The highest maximum used is 86° F. and the lowest minimum used is 50° F. For each inbred or hybrid it takes a certain number of GDUs to reach various stages of plant development.

GDU SHD=GDU TO SHED. The number of growing degree units (GDUs) or heat units required for a hybrid to have approximately 50 percent of the plants shedding pollen and is measured from the time of planting.

GDU SLK=GDU TO SILK. The number of growing degree units required for a hybrid to have approximately 50 percent of the plants with silk emergence from time of planting.

GRN QUL=QUAL.=GRAIN QUALITY. This is a 1 to 9 rating for the general quality of the shelled grain as it is harvested based on such factors as the color of the harvested grain, any mold on the grain, and any cracked grain. High scores indicate good grain quality and low scores indicate poor grain quality.

H/POP=YIELD AT HIGH DENSITY. Yield ability at relatively high plant densities on a 1–9 relative rating system with a higher number indicating the hybrid responds well to high plant densities for yield relative to other hybrids. A 1, 5, and 9 would represent very poor, average, and very good yield response, respectively, to increased plant density.

INCOME/ACRE: Relative income per acre assuming drying costs of two cents per point above 15.5 percent harvest moisture and market price of $2.75 per bushel.

INCOME ADV/ACRE: Income advantage of hybrid to be patented over other hybrid on a per acre basis.

L/POP=YIELD AT LOW DENSITY. Yield ability at relatively low plant densities on a 1–9 relative system with a higher number indicating the hybrid responds well to low plant densities for yield relative to other hybrids. A 1, 5, and 9 would represent very poor, average, and very good yield response, respectively, to low plant density.

MOIST ADV: Moisture advantage of hybrid to be patented (drier is an advantage) compared to other hybrid.

MST=MOIST=HARVEST MOISTURE. Harvest moisture is the actual percentage moisture of the grain at harvest.

MST RM=MOISTURE RM. This represents the Minnesota Relative Maturity Rating (MN RM) for the hybrid and is based on the harvest moisture of the grain relative to a standard set of checks of previously determined MN RM rating. Linear regression analysis is used to compute this rating.

P/HT=PLANT HEIGHT RATING. This is a 1–9 rating with a 1, 5, and 9 representing a very short, average, and very tall hybrid, respectively.

PLT HT=PLANT HEIGHT. This is a measure of the height of the plant from the ground to the tip of the tassel in inches.

POP K/ACRE: Plants per 0.001 acre.

PRM= PREDICTED RM. This trait, predicted relative maturity (RM), is based on the harvest moisture of the grain. The relative maturity rating is based on a known set of checks and utilizes standard linear regression analyses and is referred to as the Minnesota Relative Maturity Rating System.

P/SDG=PURPLE SEEDLING. This is an indication of purple coloring at the seedling stage. A low score indicates greater purple coloring, and a 1–9 rating system was used. Purpling can occur in cool, wet springs when the seedlings are under early season stress.

R/L=ROOT LODGING RATING. A 1–9 rating where a higher score indicates less root lodging potential (1 is very poor, 5 is intermediate, and 9 is very good, respectively, for resistance to root lodging).

ROOT (%): Percentage of plants that did not root lodge (lean greater than 30 degrees from vertical) taken on strip test plots.

RT LDG=ROOT LODGING. Root lodging is the percentage of plants that do not root lodge; plants that lean from the vertical axis at an approximately 30° angle or greater would be counted as root lodged.

S/L=STALK LODGING RATING. This is a 1–9 rating where a higher score indicates less stalk lodging potential (1 is very poor, 5 is intermediate, and 9 is very good, respectively, for resistance to stalk lodging).

SDG VGR=S/VIG=SEEDLING VIGOR. This is the visual rating (1 to 9) of the amount of vegetative growth after emergence at the seedling stage (approximately five leaves). A higher score indicates better vigor and a low score indicates poorer vigor.

SEL IND=SELECTION INDEX. The selection index gives a single measure of the hybrid's worth based on information for up to five traits. A corn breeder may utilize his or her own set of traits for the selection index. One of the traits that is almost always included is yield. The selection index data presented in the tables represent the mean value averaged across testing stations.

STA GRN=STGR=STAY GREEN. Stay green is the measure of plant health near the time of black layer formation (physiological maturity) using a 1–9 visual rating. A high score indicates better late-season plant health and a low score indicates poor plant health.

STAND (%): Percentage of plants that did not break (lodge) below the ear taken on strip test plots.

STK LDG=STALK LODGING. This is the percentage of plants that did not stalk lodge (stalk breakage) as measured by either natural lodging or pushing the stalks and determining the percentage of plants that break below the ear.

T/WT=TEST WEIGHT RATING. This is a 1–9 relative rating with a 1, 5, and 9 indicating very low, average, and very high test weight, respectively.

TST WTA=TEST WEIGHT. The measure of the weight of the grain in pounds for a given volume (bushel) adjusted for percent moisture.

WINS (%): For yield, moisture, and income, it would be the percentage of comparisons that the hybrid to be patented yielded more, had lower harvest moisture percentage, or had greater income per acre, respectively.

YLD=YIELD FOR MATURITY. This represents a 1–9 rating for a hybrid's yield potential. 1, 5, and 9 would represent very poor, average, and very high yield potential, respectively, relative to other hybrids of a similar maturity.

YLD ADV: Yield advantage (bushels per acre) of the hybrid to be patented compared to another hybrid.

DETAILED DESCRIPTION OF THE INVENTION

Pioneer hybrid 3189 is a single cross, yellow endosperm, dent corn hybrid that is best adapted across a wide region of the Corn Belt. Because it is later maturing, it will not be able to move north as well as some other hybrids. 3189 is an attractive hybrid with a very good record for high yield, stress tolerance, good stalk and root quality and excellent late season plant health or stay green. It is a short statured hybrid that flowers early and black layers late for its harvest moisture. 3189 is capable of yielding well over a wide range of environment. It performs especially well in high yield situations but also does well under stress. This hybrid will work across the Corn Belt but is susceptible to Gray leaf spot.

This hybrid has the following characteristics based on descriptive data collected primarily at Johnston, Iowa.

Type: Dent  Region Best Adapted: Most Regions, except North
Hybrid = Pioneer brand 3189
A. Maturity:
   MN Relative Maturity Rating (harvest moisture): 127
   GDU's to Physiological Maturity (black layer): 2965
   GDU's to 50% Silk: 1504

$$\text{HEAT UNITS} = \frac{[\text{Max. Temp. } (\leq 86° \text{F.}) + \text{Min. Temp } (\geq 50° \text{F.})]^*}{2} - 50$$

* If maximum is greater than 86 degrees fahrenheit, then 86 is used and if minimum is less than 50, then 50 is used. Heat units accumulated daily and can not be less than 0.

B. Plant Characteristics:
   Plant height (to tassel tip): 251 cm
   Length of top ear internode: 15 cm
   Number of ears per stalk: Single with two-ear tendency
   Ear height (to base of top ear): 107 cm
   Number of tillers: None
   Cytoplasm type: Normal
C. Leaf:
   Color: (WF9) Medium green
   Angle from Stalk: <30 degrees
   Marginal Waves: (OH7L) Many
   Number of Leaves (mature plants): 18
   Sheath Pubescence: (W22) Light
   Longitudinal Creases: (OH56A) Few
   Length (Ear node leaf): 91 cm
   Width (widest point, ear node leaf): 10 cm
D. Tassel:
   Number lateral branches: 8
   Branch Angle from central spike: <45 degrees
   Pollen Shed: Heavy
   Peduncle Length (top leaf to basal branches): 25 cm
   Anther Color: Pink
   Glume Color: Green
E. Ear (Husked Ear Data Except When Stated Otherwise):
   Length: 20 cm
   Weight: 181 gm
   Mid-point Diameter: 46 mm
   Silk Color: Green
   Husk Extension (Harvest stage): Short (ears exposed)
   Husk Leaf: Long (>15 cm)
   Taper of Ear: Slight taper
   Position of Shank (dry husks): Upright
   Kernel Rows: Straight, distinct, Number = 16
   Husk Color (fresh): Light green
   Husk Color (dry): Buff
   Shank Length: 14 cm
   Shank (No. of internodes): 7
F. Kernel (Dried):
   Size (from ear mid-point)
   Length: 12 mm
   Width: 8 mm
   Thick: 4 mm
   Shape Grade (% rounds): <20 percent
   Pericarp Color: Colorless
   Aleurone Color: Homozygous yellow
   Endosperm Color: Yellow
   Endosperm Type: Normal Starch
   Gm Wt/100 Seeds (unsized): 27 gm
G. Cob:
   Diameter at mid-point: 25 mm
   Strength: Strong
   Color: Red
H. Diseases:
   Corn Lethal Necrosis (MCMV = Maize Chlorotic Mottle Virus and MDMV = Maize Dwarf Mosaic Virus): Intermediate Maize Dwarf Mosaic Complex (MDMV & MCDV = Maize Chlorotic Dwarf Virus): Susceptible
   Anthracnose Stalk Rot (*C. Graminicola*): Intermediate
   S. Leaf Blight (*H. Maydis*): Intermediate
   N. Leaf Blight (*H. Turcicum*): Intermediate
   Common Rust (*P. Sorghi*): Intermediate -continued Gray Leaf Spot (*C. Zeae*): Susceptible
Stewarts Wilt (*E. Stewartii*): Intermediate
Goss's Wilt (*C. Nebraskense*): Resistant
Common Smut (*U. Maydis*): Intermediate
Head Smut (*S. Reiliana*): Resistant
Downy Mildew (*S. Sorghi*): Resistant
Fusarium Ear mold (*F. Moniliforme*): Intermediate
I. Insects:
   European Corn Borer-1 Leaf Damage (Pre-Flowering): Susceptible
   European Corn Borer-2 (Post Flowering): Intermediate
J. Variety Most Closely Resembling:
   Character         Hybrid
   Maturity          Pioneer Brand 3181
   Usage             Pioneer Brand 3379

Items B, C, D, E, F, & G are based on a maximum of three reps of data from Johnston, Iowa in 1987 and 1988.

This invention includes the hybrid corn seed of 3189, the hybrid corn plant produced from the hybrid corn seed, and variants, mutants, and modifications of 3189. This invention also relates to the use of 3189 in producing three-way and double cross hybrids.

The terms variant, trivial modification, and mutant refer to a hybrid seed or a plant produced by that hybrid seed which is phenotypically similar to 3189.

As used herein, the term "plant" includes plant cells, plant protoplasts, plant cell or tissue culture from which corn plants can be regenerated, plant calli, plant clumps and plant cells that are intact in plants or parts of plants, such as flowers, kernels, ears, cobs, leaves, husks, stalks and the like.

Tissue culture of corn is described in European Patent Application, publication number 160,390, incorporated herein by reference. Corn tissue culture procedures are also described in Green and Rhodes, "Plant Regeneration in Tissue Culture of Maize," *Maize for Biological Research*, (Plant Molecular Biology Association, Charlottesville, Va. 1982) at 367–372.

USES OF CORN

Corn is used as human food, livestock feed, and as raw material in industry. The food uses of corn, in addition to human consumption of corn kernels, include both products of dry- and wet-milling industries. The principal products of corn dry milling are grits, meal and flour. The corn wet-milling industry can provide starch, syrups, and dextrose for food use. Corn oil is recovered from corn germ, which is a by-product of both dry- and wet-milling industries.

Corn is also used extensively as livestock feed primarily to beef cattle, dairy cattle, hogs, and poultry.

Industrial uses of corn are mainly from corn starch from the wet-milling industry and corn flour from the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds, and other mining applications.

Plant parts other than the grain of corn are also used in industry. Stalks and husks are made into paper and wallboard and cobs are used for fuel, to make charcoal.

The seed of 3189, the hybrid corn plant produced from the seed, and various parts of the hybrid corn plant can be utilized for human food, livestock feed, and as a raw material in industry.

EXAMPLE 1

Research Comparisons for Pioneer Hybrid 3189

Comparisons of the characteristics for 3189 were made against Pioneer® brand hybrids 3379, 3295, 3269, 3181, 3168, 3140, 3320. Pioneer hybrids 3295, 3140, and 3320 are important hybrids in the Southeast of similar maturity. Pioneer hybrids 3379, 3295, 3269, 3181 and 3168 are important hybrids in the Western areas where hybrid 3180 is adapted. Pioneer hybrid 3379 is also a very significant hybrid in the central Corn Belt while Pioneer hybrid 3295 is important in the East; both are grown in areas where 3180 is adapted. These results are shown in Tables 1A–1G. Table 1A compares 3189 to Pioneer® brand hybrid 3379. 3189 is later maturing than 3379 and has very similar yield. 3189 also has better resistance to stalk lodging and has advantages over 3379 for several other important agronomic characteristics. The results in Table 1B compare 3189 to Pioneer® brand hybrid 3295. 3189 flowers earlier than 3295 but is later for grain harvest moisture. Although 3189 has a slightly lower yield than 3295 it has better resistance to stalk and root lodging, is much shorter, and is better for other important agronomic characteristics. The results in Table 1C compare 3189 to Pioneer® brand hybrid 3269. These two hybrids flower at approximately the same time but 3189 is somewhat later for grain harvest moisture maturity. 3189 has 6% higher yield than 3269 and is better than 3269 in such areas as resistance to stalk and root lodging, brittle stalk breakage resistance, and other agronomic characteristics. The results in Table 1D compare 3189 to Pioneer® brand hybrid 3181. These hybrids are in the same maturity range. 3189 has a slight yield advantage over 3181 and a significant advantage over 3181 for resistance to stalk and root lodging and several other important agronomic characteristics. The results in Table 1E compare 3189 and to Pioneer® brand hybrid 3168. 3189 flowers earlier than 3168 and at harvest has a little drier grain. These two hybrids have essentially the same bushel per acre yield but 3189 has the advantage over 3168 in the areas of resistance to stalk lodging, better stay green, and dropped ear resistance. The results in Table 1F compare Pioneer® brand hybrid 3189 to 3140. These results indicate that 3189 flowers considerably earlier than 3140, and has a little drier grain at harvest. 3189 had lower yield than 3140 but has advantages over 3140 in the areas of resistance to stalk and particularly root lodging, grain test weight and other important agronomic characteristics. The results in Table 1G compare 3189 to Pioneer® brand hybrid 3320. These results show that Pioneer® brand hybrid 3189 flowers earlier and has a little drier grain at harvest than 3320. 3189 has a slight yield advantage over 3320 and has a highly significant advantage over 3320 in the areas of resistance to stalk and root lodging. 3189 also has better stay green, test weight and is much shorter than 3320. Table 1H and Table 1I compare Pioneer® brand hybrid 3189 to DeKalb-Pfizer hybrids DK656 and DK689. DK689 and DK656 are important competitive hybrids in the Southeast and more western areas, respectively. The results show that 3189 flowers earlier than DK656 and DK689 and has a similar grain harvest moisture to DK689 but higher grain harvest moisture than DK656. 3189 had a yield advantage over both DK656 and DK689. It also was better than DK656 and DK689 for stalk lodging and other traits of agronomic importance.

TABLE 1A

HYBRID #1 - 3189
HYBRID #2 - 3379

\* = 10% SIG + = 5% SIG # = 1% SIG

| YEAR | REGION | VAR # | PRM | SEL IND | BU ACR ABS | BU ACR % MN | MST ABS | GDU SHD ABS | STK LDG ABS | RT LDG ABS | BAR PLT ABS | STA GRN ABS |
|---|---|---|---|---|---|---|---|---|---|---|---|---|
| TOTAL SUM | | 1 | 127 | 103 | 142.5 | 103 | 22.1 | 142.8 | 97.0 | 95.4 | 95.7 | 6.7 |
| | | 2 | 121 | 107 | 141.7 | 104 | 19.6 | 141.9 | 94.6 | 95.4 | 97.0 | 5.8 |
| | | LOCS | 39 | 42 | 175 | 175 | 175 | 45 | 150 | 95 | 37 | 115 |
| | | DIFF | 6 | 4 | 0.8 | 0 | 2.5 | 0.9 | 2.4 | 0.1 | 1.4 | 0.8 |
| | | PROB | .000# | .008# | .475 | .714 | .000# | .097* | .000# | .944 | .082* | .000# |

| YEAR | REGION | VAR # | TST WTA ABS | COB SC ABS | GRN QUL ABS | SDG VGR ABS | EST CNT ABS | PLT HT ABS | EAR HT ABS | DRP EAR ABS | BRT STK ABS |
|---|---|---|---|---|---|---|---|---|---|---|---|
| TOTAL SUM | | 1 | 57.9 | 6.7 | 7.2 | 6.1 | 58.8 | 100.0 | 41.4 | 99.9 | 95.4 |
| | | 2 | 57.5 | 6.7 | 7.3 | 6.0 | 61.8 | 102.3 | 43.9 | 99.7 | 96.1 |
| | | LOCS | 170 | 17 | 78 | 76 | 99 | 94 | 95 | 81 | 16 |
| | | DIFF | 0.5 | 0.1 | 0.1 | 0.0 | 3.0 | 2.3 | 2.5 | 0.2 | 0.7 |
| | | PROB | .000# | .792 | .515 | .870 | .000# | .000# | .000# | .019+ | .470 |

TABLE 1B

HYBRID #1 - 3189
HYBRID #2 - 3295

\* = 10% SIG + = 5% SIG # = 1% SIG

| YEAR | REGION | VAR # | PRM | SEL IND | BU ACR ABS | BU ACR % MN | MST ABS | GDU SHD ABS | STK LDG ABS | RT LDG ABS | BAR PLT ABS | STA GRN ABS |
|---|---|---|---|---|---|---|---|---|---|---|---|---|
| TOTAL SUM | | 1 | 127 | 99 | 142.2 | 101 | 21.6 | 143.2 | 96.4 | 94.9 | 96.0 | 6.3 |
| | | 2 | 123 | 106 | 145.7 | 103 | 20.1 | 147.4 | 94.7 | 88.7 | 95.7 | 5.3 |
| | | LOCS | 45 | 39 | 224 | 224 | 224 | 54 | 192 | 104 | 61 | 145 |
| | | DIFF | 3 | 6 | 3.5 | 2 | 1.5 | 4.2 | 1.7 | 6.1 | 0.3 | 1.0 |
| | | PROB | .000# | .029+ | .006# | .076* | .000# | .000# | .002# | .000# | .631 | .000# |

| YEAR | REGION | VAR # | TST WTA ABS | COB SC ABS | GRN QUL ABS | SDG VGR ABS | EST CNT ABS | PLT HT ABS | EAR HT ABS | DRP EAR ABS | BRT STK ABS |
|---|---|---|---|---|---|---|---|---|---|---|---|
| TOTAL SUM | | 1 | 58.0 | 6.7 | 6.8 | 5.7 | 58.7 | 100.5 | 42.2 | 99.8 | 92.2 |
| | | 2 | 57.1 | 6.1 | 7.0 | 6.8 | 60.8 | 109.6 | 47.6 | 98.8 | 95.2 |
| | | LOCS | 214 | 28 | 124 | 117 | 172 | 118 | 119 | 98 | 35 |
| | | DIFF | 0.9 | 0.6 | 0.1 | 1.0 | 2.1 | 9.1 | 5.4 | 1.0 | 3.0 |
| | | PROB | .000# | .006# | .245 | .000# | .000# | .000# | .000# | .000# | .015+ |

TABLE 1C

HYBRID #1 - 3189
HYBRID #2 - 3269

\* = 10% SIG + = 5% SIG # = 1% SIG

| YEAR | REGION | VAR # | PRM | SEL IND | BU ACR ABS | BU ACR % MN | MST ABS | GDU SHD ABS | STK LDG ABS | RT LDG ABS | BAR PLT ABS | STA GRN ABS |
|---|---|---|---|---|---|---|---|---|---|---|---|---|
| TOTAL SUM | | 1 | 127 | 105 | 160.7 | 104 | 21.4 | 140.1 | 97.4 | 95.3 | 96.3 | 6.9 |
| | | 2 | 124 | 102 | 152.8 | 99 | 20.1 | 140.9 | 96.4 | 92.5 | 97.0 | 5.5 |
| | | LOCS | 24 | 18 | 100 | 100 | 100 | 27 | 84 | 54 | 36 | 73 |
| | | DIFF | 3 | 3 | 7.8 | 6 | 1.2 | 0.8 | 1.0 | 2.8 | 0.7 | 1.4 |
| | | PROB | .000# | .261 | .000# | .000# | .000# | .171 | .052* | .003# | .101 | .000# |

| | | VAR | TST WTA | COB SC | GRN QUL | SDG VGR | EST CNT | PLT HT | EAR HT | DRP EAR | BRT STK |
|---|---|---|---|---|---|---|---|---|---|---|---|

TABLE 1C-continued

| YEAR | REGION | # | ABS | ABS | ABS | ABS | ABS | ABS | ABS | ABS | ABS |
|---|---|---|---|---|---|---|---|---|---|---|---|
| TOTAL SUM | | 1 | 58.6 | 6.6 | 7.6 | 5.6 | 65.3 | 105.4 | 43.8 | 99.8 | 92.3 |
| | | 2 | 59.0 | 6.3 | 8.0 | 5.9 | 68.9 | 108.5 | 45 | 99.0 | 85.0 |
| | | LOCS | 99 | 14 | 16 | 54 | 74 | 57 | 56 | 55 | 36 |
| | | DIFF | 0.4 | 0.3 | 0.4 | 0.3 | 3.6 | 3.1 | 1.1 | 0.8 | 7.4 |
| | | PROB | .000# | .206 | .085* | .077* | .000# | .000# | .021+ | .000# | .000# |

TABLE 1D

HYBRID #1 - 3189
HYBRID #2 - 3181

\* = 10% SIG + = 5% SIG # = 1% SIG

| YEAR | REGION | VAR # | PRM | SEL IND | BU ACR ABS | BU ACR % MN | MST ABS | GDU SHD ABS | STK LDG ABS | RT LDG ABS | BAR PLT ABS | STA GRN ABS |
|---|---|---|---|---|---|---|---|---|---|---|---|---|
| TOTAL SUM | | 1 | 127 | 104 | 153.4 | 103 | 21.8 | 140.5 | 97.3 | 97.5 | 95.7 | 6.6 |
| | | 2 | 126 | 102 | 151.1 | 100 | 21.6 | 142.2 | 95.2 | 92.3 | 95.8 | 4.6 |
| | | LOCS | 33 | 25 | 152 | 152 | 152 | 41 | 135 | 72 | 50 | 106 |
| | | DIFF | 1 | 2 | 2.3 | 2 | 0.2 | 1.6 | 2.1 | 5.2 | 0.0 | 2.0 |
| | | PROB | .079* | .148 | .114 | .087* | .032+ | .000# | .000# | .000# | .985 | .000# |

| YEAR | REGION | VAR # | TST WTA ABS | COB SC ABS | GRN QUL ABS | SDG VGR ABS | EST CNT ABS | PLT HT ABS | EAR HT ABS | DRP EAR ABS | BRT STK ABS |
|---|---|---|---|---|---|---|---|---|---|---|---|
| TOTAL SUM | | 1 | 58.3 | 6.5 | 6.6 | 5.5 | 61.7 | 104.4 | 43.6 | 99.8 | 91.9 |
| | | 2 | 58.2 | 5.8 | 6.7 | 5.6 | 61.8 | 110.5 | 48.1 | 99.4 | 90.7 |
| | | LOCS | 151 | 18 | 49 | 78 | 117 | 88 | 87 | 76 | 32 |
| | | DIFF | 0.1 | 0.7 | 0.2 | 0.2 | 0.1 | 6.2 | 4.4 | 0.4 | 1.2 |
| | | PROB | .257 | .007# | .346 | .234 | .748 | .000# | .000# | .001# | .285 |

TABLE 1E

HYBRID #1 - 3189
HYBRID #2 - 3168

\* = 10% SIG + = 5% SIG # = 1% SIG

| YEAR | REGION | VAR # | PRM | SEL IND | BU ACR ABS | BU ACR % MN | MST ABS | GDU SHD ABS | STK LDG ABS | RT LDG ABS | BAR PLT ABS | STA GRN ABS |
|---|---|---|---|---|---|---|---|---|---|---|---|---|
| TOTAL SUM | | 1 | 127 | 104 | 161.3 | 104 | 21.2 | 139.6 | 97.9 | 95.2 | 97.7 | 6.8 |
| | | 2 | 128 | 102 | 161.3 | 103 | 21.6 | 144.1 | 96.2 | 93.7 | 97.6 | 5.3 |
| | | LOCS | 27 | 25 | 115 | 115 | 115 | 29 | 97 | 60 | 33 | 77 |
| | | DIFF | 1 | 2 | 0.0 | 1 | 0.3 | 4.5 | 1.7 | 1.5 | 0.1 | 1.5 |
| | | PROB | .131 | .344 | .998 | .605 | .007# | .000# | .006# | .257 | .856 | .000# |

| YEAR | REGION | VAR # | TST WTA ABS | COB SC ABS | GRN QUL ABS | SDG VGR ABS | EST CNT ABS | PLT HT ABS | EAR HT ABS | DRP EAR ABS | BRT STK ABS |
|---|---|---|---|---|---|---|---|---|---|---|---|
| TOTAL SUM | | 1 | 58.3 | 6.6 | 7.2 | 5.6 | 65.6 | 106.3 | 44.4 | 99.9 | 93.0 |
| | | 2 | 59.5 | 6.6 | 7.4 | 5.5 | 67.6 | 109.4 | 47.5 | 99.6 | 95.8 |
| | | LOCS | 109 | 14 | 19 | 47 | 68 | 67 | 66 | 49 | 32 |
| | | DIFF | 1.1 | 0.1 | 0.2 | 0.1 | 2.0 | 1.1 | 3.0 | 0.3 | 2.9 |
| | | PROB | .000# | .702 | .291 | .424 | .001# | .000# | .000# | .035+ | .027+ |

TABLE 1F

HYBRID #1 - 3189
HYBRID #2 - 3140

\* = 10% SIG + = 5% SIG # = 1% SIG

| YEAR | REGION | VAR # | PRM | SEL IND | BU ACR ABS | BU ACR % MN | MST ABS | GDU SHD ABS | STK LDG ABS | RT LDG ABS | BAR PLT ABS | STA GRN ABS |
|---|---|---|---|---|---|---|---|---|---|---|---|---|
| TOTAL SUM | | 1 | 127 | 101 | 135.0 | 100 | 20.3 | 147.6 | 96.0 | 95.5 | 97.7 | 6.0 |
| | | 2 | 128 | 104 | 143.9 | 107 | 20.7 | 153.4 | 94.5 | 81.2 | 98.6 | 6.1 |
| | | LOCS | 19 | 18 | 103 | 103 | 103 | 15 | 85 | 42 | 16 | 76 |
| | | DIFF | 2 | 3 | 8.9 | 7 | 0.5 | 5.9 | 1.5 | 14.3 | 0.9 | 0.1 |
| | | PROB | .001# | .289 | .000# | .000# | .001# | .000# | .028+ | .000# | .167 | .498 |

| YEAR | REGION | VAR # | TST WTA ABS | COB SC ABS | GRN QUL ABS | SDG VGR ABS | EST CNT ABS | PLT HT ABS | EAR HT ABS | DRP EAR ABS | BRT STK ABS |
|---|---|---|---|---|---|---|---|---|---|---|---|
| TOTAL SUM | | 1 | 58.2 | 7.8 | 7.0 | 6.0 | 54.4 | 103.2 | 42.7 | 99.9 | 97.4 |
| | | 2 | 56.8 | 7.1 | 7.0 | 5.0 | 51.7 | 113.4 | 49.5 | 99.3 | 98.4 |
| | | LOCS | 96 | 8 | 75 | 53 | 56 | 56 | 56 | 18 | 2 |
| | | DIFF | 1.3 | 0.7 | 0.1 | 1.0 | 2.7 | 10.2 | 6.9 | 0.6 | 1.0 |
| | | PROB | .000# | .102 | .571 | .000# | .002# | .000# | .000# | .151 | .541 |

TABLE 1G

HYBRID #1 - 3189
HYBRID #2 - 3320

\* = 10% SIG + = 5% SIG # = 1% SIG

| YEAR | REGION | VAR # | PRM | SEL IND | BU ACR ABS | BU ACR % MN | MST ABS | GDU SHD ABS | STK LDG ABS | RT LDG ABS | BAR PLT ABS | STA GRN ABS |
|---|---|---|---|---|---|---|---|---|---|---|---|---|
| TOTAL SUM | | 1 | 126 | 96 | 144.4 | 100 | 19.5 | 145.4 | 96.0 | 96.1 | 97.8 | 5.9 |
| | | 2 | 127 | 98 | 141.7 | 98 | 19.8 | 148.1 | 89.7 | 85.9 | 97.3 | 4.5 |
| | | LOCS | 16 | 13 | 89 | 89 | 90 | 14 | 64 | 37 | 10 | 57 |
| | | DIFF | 1 | 2 | 2.7 | 2 | 0.3 | 2.7 | 6.3 | 10.2 | 0.5 | 1.4 |
| | | PROB | .012+ | .845 | .140 | .122 | .016+ | .007# | .000# | .000# | .400 | .000# |

| YEAR | REGION | VAR # | TST WTA ABS | COB SC ABS | GRN QUL ABS | SDG VGR ABS | EST CNT ABS | PLT HT ABS | EAR HT ABS | DRP EAR ABS | BRT STK ABS |
|---|---|---|---|---|---|---|---|---|---|---|---|
| TOTAL SUM | | 1 | 58.2 | 7.3 | 7.2 | 5.8 | 55.0 | 107.0 | 45.6 | 100.0 | 97.9 |
| | | 2 | 57.7 | 5.8 | 8.0 | 5.8 | 56.7 | 113.4 | 48.9 | 99.9 | 100.0 |
| | | LOCS | 79 | 10 | 50 | 40 | 43 | 43 | 44 | 6 | 1 |
| | | DIFF | 0.5 | 1.5 | 0.8 | 0.0 | 1.7 | 6.4 | 3.2 | 0.1 | 2.1 |
| | | PROB | .000# | .000# | .000# | .907 | .219 | .000# | .000# | .363 | |

TABLE 1H

HYBRID #1 - 3189
HYBRID #2 - DK656

\* = 10% SIG + = 5% SIG # = 1% SIG

| YEAR | REGION | VAR # | PRM | SEL IND | BU ACR ABS | BU ACR % MN | MST ABS | GDU SHD ABS | STK LDG ABS | RT LDG ABS | BAR PLT ABS | STA GRN ABS |
|---|---|---|---|---|---|---|---|---|---|---|---|---|
| TOTAL SUM | | 1 | 127 | 101 | 141.1 | 101 | 22.1 | 144.4 | 96.8 | 96.1 | 96.6 | 6.5 |
| | | 2 | 125 | 96 | 138.4 | 99 | 21.0 | 146.4 | 90.0 | 95.3 | 95.9 | 3.3 |
| | | LOCS | 21 | 21 | 106 | 106 | 106 | 26 | 97 | 52 | 27 | 69 |
| | | DIFF | 3 | 5 | 2.6 | 2 | 1.1 | 2.0 | 6.8 | 0.8 | 0.8 | 3.2 |
| | | PROB | .000# | .001# | .120 | .268 | .000# | .022+ | .000# | .512 | .283 | .000# |

| | | VAR | TST WTA | COB SC | GRN QUL | SDG VGR | EST CNT | PLT HT | EAR HT | DRP EAR | BRT STK |
|---|---|---|---|---|---|---|---|---|---|---|---|

TABLE 1H-continued

| YEAR | REGION | # | ABS | ABS | ABS | ABS | ABS | ABS | ABS | ABS | ABS |
|------|--------|---|-----|-----|-----|-----|-----|-----|-----|-----|-----|
| TOTAL SUM | | 1 | 58.0 | 7.6 | 7.1 | 6.1 | 58.4 | 96.8 | 40.3 | 99.9 | 97.9 |
| | | 2 | 57.3 | 7.7 | 6.8 | 5.5 | 57.2 | 101.6 | 46.0 | 99.7 | 97.9 |
| | | LOCS | 106 | 10 | 59 | 55 | 82 | 56 | 56 | 35 | 1 |
| | | DIFF | 0.7 | 0.2 | 0.2 | 0.6 | 1.3 | 4.7 | 5.7 | 0.2 | 0.0 |
| | | PROB | .000# | .679 | .174 | .000# | .017+ | .000# | .000# | .057* | |

TABLE 1I

HYBRID #1 - 3189
HYBRID #2 - DK689

\* = 10% SIG  + = 5% SIG  # = 1% SIG

| YEAR | REGION | VAR # | PRM | SEL IND | BU ACR ABS | BU ACR % MN | MST ABS | GDU SHD ABS | STK LDG ABS | RT LDG ABS | BAR PLT ABS | STA GRN ABS |
|------|--------|-------|-----|---------|-----------|-------------|---------|-------------|-------------|------------|-------------|-------------|
| TOTAL SUM | | 1 | 127 | 98 | 143.2 | 97 | 20.4 | 134.0 | 93.8 | 98.1 | 97.8 | 6.4 |
| | | 2 | 128 | 86 | 136.6 | 93 | 20.7 | 138.5 | 85.4 | 95.4 | 95.5 | 5.5 |
| | | LOCS | 6 | 6 | 33 | 33 | 33 | 4 | 21 | 12 | 2 | 24 |
| | | DIFF | 1 | 13 | 6.7 | 4 | 0.4 | 4.5 | 8.4 | 2.7 | 2.3 | 0.9 |
| | | PROB | .202 | .056* | .017+ | .034+ | .126 | .063* | .047+ | .361 | .038+ | .000# |

| YEAR | REGION | VAR # | TST WTA ABS | COB SC ABS | GRN QUL ABS | SDG VGR ABS | EST CNT ABS | PLT HT ABS | EAR HT ABS | DRP EAR ABS |
|------|--------|-------|-------------|------------|-------------|-------------|-------------|------------|------------|-------------|
| TOTAL SUM | | 1 | 57.1 | 5.5 | 5.8 | 5.8 | 52.6 | 99.9 | 42.5 | 99.8 |
| | | 2 | 56.8 | 3.5 | 7.4 | 4.6 | 51.0 | 104.9 | 48.4 | 99.8 |
| | | LOCS | 32 | 1 | 11 | 16 | 18 | 19 | 20 | 5 |
| | | DIFF | 0.3 | 2.0 | 1.6 | 1.1 | 1.6 | 5.0 | 6.0 | 0.0 |
| | | PROB | .286 | | .005# | .002# | .057* | .001# | .000# | .912 |

EXAMPLE 2

Strip Test Data for Hybrid 3189

Comparison data was collected from strip tests that were grown by farmers. Each hybrid was grown in strips of 4, 6, 8, 12, etc. rows in fields depending on the size of the planter used. The data were collected from strip tests that had the hybrids in the same area of a field. The grain was harvested from a measured area and weighed. The moisture percentage was determined to compute yield and bushels per acre was adjusted to 15.5% moisture. The number of comparisons represent the number of locations or replications where the two hybrids were grown in the same field in close proximity and compared.

Comparison strip testing was done between 3189 and Pioneer® brand hybrids 3379, 3295, 3269, 3181, 3168, 3140, 3320 and DeKalb-Pfizer hybrids DK656 and DK689.

These results are presented in Table 2. The results illustrate that Pioneer hybrid 3189 had a yield advantage over all the comparison hybrids except Pioneer® brand hybrid 3140 and DeKalb-Pfizer hybrid DK689. These yield advantages ranged from a low of 3.7 bushels per acre over Pioneer® brand hybrid 3379 to a high of 14.6 bushels per acre over DeKalb-Pfizer hybrid DK656. This yield advantage resulted in a better return on the farmers investment based on adjusted gross income. 3189 showed an income advantage to the farmer over all the comparison hybrids except Pioneer® brand hybrid 3140 and DeKalb-Pfizer hybrid DK689. This income advantage ranged from a low of $2.92 per acre over Pioneer® brand hybrid 3379 to a high of $36.03 per acre over DK656. More extensive research data in the South shows a yield advantage of 3189 over DK689. The strip test data supports the use of 3189 as an important hybrid in the southern Corn Belt.

TABLE 2

Pioneer Hybrid 3189 vs Pioneer Hybrids 3379, 3295, 3269, 3181, 3168, 3140, 3320, and Dekalb Hybrids DK656 and DK689 from 1988 Strip Test

| Brand | Product | Yield | Yld Adv | Wins (%) | Moist | Moist Adv | Wins (%) | Income /Acre | Inc Adv | Wins (%) | Pop K/ Acre | Stand (%) | Roots (%) | Tst Wt |
|-------|---------|-------|---------|----------|-------|-----------|----------|--------------|---------|----------|-------------|-----------|-----------|--------|
| PIONEER | 3189 | 134.8 | 3.7 | 63 | 21.6 | −2.5 | 7 | 353.58 | 2.92 | 56 | 23.4 | 96 | 98 | 56.7 |
| PIONEER | 3379 | 131.1 | | | 19.1 | | | 350.66 | | | 23.5 | 96 | 98 | 57.0 |
| COMPARISONS | | 292 | | | 292 | | | 292 | | | 184 | 141 | 130 | 220 |
| PIONEER | 3189 | 128.8 | 5.5 | 66 | 21.9 | −1.5 | 17 | 337.52 | 10.74 | 63 | 23.0 | 96 | 97 | 56.3 |

TABLE 2-continued

Pioneer Hybrid 3189 vs Pioneer Hybrids 3379, 3295, 3269, 3181, 3168, 3140, 3320,
and Dekalb Hybrids DK656 and DK689
from 1988 Strip Test

| Brand | Product | Yield | Yld Adv | Wins (%) | Moist | Moist Adv | Wins (%) | Income /Acre | Inc Adv | Wins (%) | Pop K/ Acre | Stand (%) | Roots (%) | Tst Wt |
|---|---|---|---|---|---|---|---|---|---|---|---|---|---|---|
| PIONEER | 3295 | 123.3 | | | 20.4 | | | 326.78 | | | 22.8 | 94 | 95 | 56.2 |
| COMPARISONS | | 304 | | | 304 | | | 304 | | | 185 | 108 | 94 | 200 |
| PIONEER | 3189 | 133.0 | 7.1 | 70 | 20.4 | −1.5 | 17 | 351.46 | 14.26 | 64 | 21.6 | 97 | 99 | 56.8 |
| PIONEER | 3269 | 125.9 | | | 18.9 | | | 337.20 | | | 20.9 | 97 | 99 | 57.6 |
| COMPARISONS | | 118 | | | 118 | | | 118 | | | 63 | 61 | 61 | 112 |
| PIONEER | 3189 | 132.0 | 7.6 | 72 | 20.6 | −0.6 | 34 | 349.19 | 18.05 | 71 | 22.3 | 95 | 95 | 57.1 |
| PIONEER | 3181 | 124.4 | | | 20.0 | | | 331.14 | | | 22.3 | 95 | 97 | 56.9 |
| COMPARISONS | | 104 | | | 104 | | | 104 | | | 60 | 52 | 52 | 91 |
| PIONEER | 3189 | 170.6 | 9.3 | 83 | 21.1 | 0.0 | 44 | 447.68 | 24.55 | 83 | 24.7 | 97 | 99 | 57.4 |
| PIONEER | 3168 | 161.3 | | | 21.1 | | | 423.13 | | | 24.5 | 97 | 99 | 58.4 |
| COMPARISONS | | 118 | | | 118 | | | 118 | | | 87 | 86 | 85 | 116 |
| PIONEER | 3189 | 126.6 | −2.6 | 48 | 20.7 | 0.5 | 69 | 334.33 | −6.05 | 47 | 23.2 | 95 | 97 | 56.0 |
| PIONEER | 3140 | 129.2 | | | 21.2 | | | 340.38 | | | 22.2 | 93 | 95 | 55.8 |
| COMPARISONS | | 143 | | | 143 | | | 143 | | | 95 | 53 | 44 | 97 |
| PIONEER | 3189 | 131.3 | 6.1 | 69 | 20.2 | 0.3 | 62 | 348.50 | 16.97 | 70 | 23.1 | 95 | 98 | 56.7 |
| PIONEER | 3320 | 125.2 | | | 20.5 | | | 331.53 | | | 22.5 | 93 | 98 | 56.8 |
| COMPARISONS | | 98 | | | 98 | | | 98 | | | 64 | 36 | 30 | 72 |
| PIONEER | 3189 | 111.4 | 14.6 | 82 | 21.2 | −1.1 | 28 | 293.96 | 36.03 | 80 | 20.4 | 90 | 89 | 56.3 |
| DEKALB-PFIZER | DK656 | 96.8 | | | 20.1 | | | 257.93 | | | 20.4 | 89 | 93 | 56.0 |
| COMPARISONS | | 46 | | | 46 | | | 46 | | | 36 | 21 | 21 | 29 |
| PIONEER | 3189 | 106.7 | −4.4 | 42 | 20.5 | 0.8 | 57 | 281.15 | −11.10 | 42 | 22.4 | 93 | 100 | 54.9 |
| DEKALB-PFIZER | DK689 | 111.1 | | | 21.3 | | | 292.25 | | | 22.8 | 82 | 100 | 55.2 |
| COMPARISONS | | 7 | | | 7 | | | 7 | | | 7 | 2 | 1 | 7 |

EXAMPLE 3

Comparison of Key Characteristics for Hybrid 3189

Characteristics of hybrid 3189 are compared to Pioneer® brand hybrids 3379, 3295, 3269, 3181, 3168, 3140, 3320, and DeKalb-Pfizer DK656 and DK689 in Table 3. The ratings given for most of the traits are on a 1–9 basis. In these cases 9 would be outstanding while a 1 would be poor for the given characteristics. These values are based on performance of the given hybrid relative to other Pioneer® commercial and precommercial hybrids that are grown in the trials. These traits characterized in Table 3 were defined previously and the ratings utilized not only research data but experience that trained corn researchers had in the field as well as sales experience with the hybrids in strip test and the field. These scores reflect the hybrids relative performance to other hybrids for the characteristics listed. The Table shows that hybrid 3189 has excellent yield for its maturity and at high plant densities, good stalk and root lodging resistance, excellent stay green, excellent drouth tolerance and is relatively short and low eared compared to the other hybrids.

TABLE 3

HYBRID PATENT COMPARISONS-CHARACTERISTICS
Pioneer Hybrid 3189 VS Pioneer Hybrids 3379, 3295, 3269, 3181, 3168, 3140, 3320, and DEKALB DK656 and DK689

| HYBRID | MST RM | GDU BL | GDU SLK | YLD | H/POP | L/POP | D/D | S/L | R/L | STGR | D/T | T/WT | COB | QUAL. |
|---|---|---|---|---|---|---|---|---|---|---|---|---|---|---|
| 3189 | 127 | 2965 | 1504 | 8 | 8 | 6 | 8 | 7 | 7 | 8 | 8 | 6 | 7 | 4 |
| 3379 | 119 | 2873 | 1483 | 9 | 9 | 6 | 8 | 7 | 5 | 9 | 8 | 5 | 5 | 5 |
| 3295 | 123 | 2841 | 1533 | 7 | 6 | 7 | 6 | 6 | 4 | 8 | 4 | 4 | 4 | 4 |
| 3269 | 124 | 2848 | 1477 | 6 | 7 | 6 | 6 | 6 | 6 | 7 | 7 | 6 | 6 | 6 |
| DK656 | 125 | 2821 | 1494 | 7 | 7 | 8 | 5 | 4 | 3 | 2 | 7 | 5 | 6 | 4 |
| 3181 | 127 | 2879 | 1484 | 6 | 6 | 8 | 6 | 5 | 3 | 4 | 4 | 6 | 4 | 4 |
| 3168 | 128 | 2861 | 1472 | 7 | 8 | 7 | 5 | 6 | 6 | 5 | 5 | 8 | 8 | 9 |
| DK689 | 128 | — | — | 4 | 4 | 5 | — | 4 | 5 | 7 | 4 | 5 | 3 | 7 |
| 3140 | 129 | 2955 | 1585 | 7 | 6 | 8 | 6 | 6 | 4 | 8 | 6 | 3 | 3 | 4 |
| 3320 | 129 | 2887 | 1568 | 6 | 4 | 7 | 6 | 4 | 3 | 4 | 7 | 5 | 3 | 8 |

| HYBRID | P/SDG | S/VIG | ESC | P/HT | E/HT | D/E | B/SIK |
|---|---|---|---|---|---|---|---|
| 3189 | 6 | 4 | 4 | 3 | 3 | 6 | 6 |
| 3379 | 3 | 4 | 5 | 4 | 4 | 5 | 8 |

TABLE 3-continued

| | | | | | | | |
|---|---|---|---|---|---|---|---|
| 3295 | 6 | 8 | 6 | 8 | 8 | 3 | 5 |
| 3269 | 6 | 5 | 6 | 5 | 4 | 4 | 3 |
| DK656 | — | 4 | 5 | 4 | 8 | 5 | 8 |
| 3181 | 7 | 5 | 4 | 6 | 5 | 5 | 3 |
| 3168 | 6 | 5 | 6 | 4 | 5 | 5 | 7 |
| DK689 | — | 3 | 4 | 4 | 5 | — | — |
| 3140 | 6 | 3 | 4 | 7 | 8 | 4 | 5 |
| 3320 | 6 | 6 | 5 | 6 | 6 | 5 | 8 |

Although the foregoing invention has been described in some detail by way of illustration and example for purposes of clarity and understanding, it will be obvious that certain changes and modifications may be practiced within the scope of the invention, as limited only by the scope of the appended claims.

DEPOSITS

Applicant has made a deposit of at least 2500 seeds of corn hybrid 3189 (as described herein) with the American Type Culture Collection (ATCC), Rockville, Md. 20852 USA, ATCC Accession No. 75942. The seeds deposited with the ATCC on Nov. 3, 1994 were taken from the deposit maintained by Pioneer Hi-Bred International, Inc., 700 Capital Square, 400 Locust Street, Des Moines, Iowa 50309-2340 since prior to the filing date of this application. This deposit of the corn hybrid 3189 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has satisfied all the requirements of 37 C.F.R. §§1.801–1.809, including providing an indication of the viability of the sample. Applicant imposes no restrictions on the availability of the deposited material from the ATCC; however, Applicant has no authority to waive any restrictions imposed by law on the transfer of biological material or its transportation in commerce. Applicant does not waive any infringement of rights granted under this patent.

What is claimed is:

1. A hybrid corn plant designated as 3189 and having ATCC Accession No. 75942, and its parts.

2. A plant part according to claim 1, selected from the group consisting of leaves, pollen, embryos, protoplasts meristematic cells, roots, root tips, anthers, silk, flowers, kernels, ears, cobs, husks, stalks and cells and organelles thereof.

3. A tissue culture of cells of a plant part of claim 2.

4. A tissue culture according to claim 3 comprising regenerable cells of a plant part selected from meristematic tissue, anthers, leaves, embryos and pollen, and protoplasts thereof.

5. A corn plant and its parts regenerated from the regenerable cells of the tissue culture of claim 3.

* * * * *